(12) United States Patent
Kytönen et al.

(10) Patent No.: US 12,016,708 B2
(45) Date of Patent: Jun. 25, 2024

(54) X-RAY IMAGING APPARATUS

(71) Applicant: PLANMECA OY, Helsinki (FI)

(72) Inventors: Aapo Kytönen, Helsinki (FI); Tommi Huomo, Helsinki (FI); Harri Karppi, Helsinki (FI)

(*) Notice: Subject to any disclaimer, the term of this patent is extended or adjusted under 35 U.S.C. 154(b) by 284 days.

(21) Appl. No.: 17/615,965

(22) PCT Filed: Apr. 8, 2020

(86) PCT No.: PCT/EP2020/060100
§ 371 (c)(1),
(2) Date: Dec. 2, 2021

(87) PCT Pub. No.: WO2020/254006
PCT Pub. Date: Dec. 24, 2020

(65) Prior Publication Data
US 2022/0313179 A1    Oct. 6, 2022

Related U.S. Application Data

(63) Continuation of application No. 16/714,337, filed on Dec. 13, 2019, now Pat. No. 11,684,319.

(30) Foreign Application Priority Data

| Jun. 3, 2019 | (FI) | 20190042 |
| Jul. 5, 2019 | (FI) | 20190054 |
| Dec. 13, 2019 | (FI) | 20196081 |

(51) Int. Cl.
*A61B 6/03* (2006.01)
*A61B 6/00* (2006.01)
(Continued)

(52) U.S. Cl.
CPC ............ *A61B 6/032* (2013.01); *A61B 6/4429* (2013.01); *A61B 6/4435* (2013.01);
(Continued)

(58) Field of Classification Search
CPC ..... A61B 6/032; A61B 6/4429; A61B 6/4435; A61B 6/4452; A61B 6/4476; A61B 6/587;
(Continued)

(56) References Cited

U.S. PATENT DOCUMENTS

| 2003/0048868 A1* | 3/2003 | Bailey ............... A61B 6/032 378/65 |
| 2005/0063517 A1 | 3/2005 | Karlsson et al. |

(Continued)

FOREIGN PATENT DOCUMENTS

| DE | 10337931 A1 | 3/2005 | |
| JP | 2004141656 A * | 5/2004 | ............ A61B 6/04 |

(Continued)

OTHER PUBLICATIONS

International Search Report for PCT/EP2020/060100, dated Dec. 9, 2020, 2 page.

*Primary Examiner* — Kiho Kim
(74) *Attorney, Agent, or Firm* — Lippes Mathias LLP

(57) ABSTRACT

An apparatus applicable for use in the context of dental or medical X-ray imaging includes a support construction 12 to which an X-ray source 14, an X-ray detector and a visible light emitting construction 141' are mounted. The support construction 12 is configured to enable moving the X-ray source 14 and the visible light emitting construction 141' such that they can be positioned at a given first and second time at essentially the same location so as to direct, when positioned at that location, a given field pattern in essentially the same direction towards the X-ray detector 15.

20 Claims, 9 Drawing Sheets

(51) Int. Cl.
*A61B 6/58* (2024.01)
*A61B 5/00* (2006.01)

(52) U.S. Cl.
CPC .......... *A61B 6/4452* (2013.01); *A61B 6/4476* (2013.01); *A61B 6/587* (2013.01); *A61B 5/0088* (2013.01)

(58) Field of Classification Search
CPC ....... A61B 5/0088; A61B 6/0442; A61B 6/08; A61B 6/14; A61B 6/4085; A61B 6/035; A61B 6/0487
See application file for complete search history.

(56) References Cited

U.S. PATENT DOCUMENTS

| | | | |
|---|---|---|---|
| 2007/0183565 A1 | 8/2007 | Brandstatter et al. | |
| 2009/0310749 A1* | 12/2009 | Kojima .................. | A61B 6/502 378/98.12 |
| 2018/0140270 A1* | 5/2018 | Profio .................... | A61B 5/055 |
| 2019/0046128 A1* | 2/2019 | Yamazaki .............. | A61B 6/032 |

FOREIGN PATENT DOCUMENTS

| | | | | |
|---|---|---|---|---|
| JP | 2004343921 A | * | 12/2004 | .............. A61B 6/56 |
| WO | 2005110233 A1 | | 11/2005 | |

* cited by examiner

X-RAY IMAGING APPARATUS

FIELD OF THE INVENTION

The invention relates to dental or medical radiography. In particular, to structures of an apparatus according to the invention are applicable for use in the context of dental or medical X-ray imaging.

BACKGROUND OF THE INVENTION

When exposing a living object to ionizing radiation, to generate an image of an anatomy for medical purposes, the imaging must be implemented, in view of the purpose of the imaging, by as low a radiation dose as possible to still get an image of reasonable quality.

One parameter to be considered relating to the radiation dose is the volume of the anatomy getting exposed. When not wishing to irradiate inessential parts of an anatomy, one is faced with a problem of proper relative positioning of the desired anatomy and components of the imaging apparatus.

To facilitate such positioning, e.g. various positioning lights have been used. Such lights may be configured to cast e.g. laser lines or a light field on an anatomy. In the context of radiography, a term light field-indicator is sometimes used when referring to an equipment incorporated in an X-ray imaging system which is configured to "predict" the shape and dimensions of the irradiation field during the subsequent exposure. Such systems may include components that are let to remain between the X-ray source and detector also during the imaging exposure while in some others, such components that would remain between the X-ray source and detector are moved away from the X-ray beam path before the X-ray exposure.

Computed tomography (CT) is a form of X-ray imaging in which a volume to be imaged is irradiated from different directions and, from the image information thus acquired, a desired two- or three-dimensional image can be reconstructed.

Traditional CT apparatus are large and massive, and they are typically mounted on a floor. A patient is positioned for imaging within an examination opening of the apparatus, typically on a horizontally extending and laterally movable examination platform.

Since development of cone beam computed tomography (CBCT) technology in which, for one, slower rotational speeds of the imaging means are used, apparatus of less weight than that of the more traditional CT apparatus have been developed. Among the CBCT apparatus, there also are those not designed to be mounted e.g. on the floor but constructed to be mobile.

Some of the CT apparatus designed in recent times are multipurpose apparatus supporting more than one imaging modality, like those configured to enable both 2D and 3D radiography. When having more functionalities, however, complexity of the apparatus tends to increase, e.g. as a consequence of a new kind of freedom of movement having been arranged to one or more components of the apparatus. Also the weight of the apparatus may then increase while some modifications may generate new challenges relating to getting an anatomy positioned for an exposure.

BRIEF DESCRIPTION OF THE INVENTION

The object of the invention is a medical or dental X-ray imaging apparatus, in one particular embodiment a CBCT apparatus, with novel features relating to mutual positioning of the imaging means of the apparatus and an anatomy for an imaging exposure.

The characteristic features of the invention are defined in claim 1. More particularly, those features include the apparatus of the present disclosure being configured to enable a light field indicator system to cast a visible light field pattern from essentially the same location as from where an X-ray beam generating system emits an X-ray irradiation beam during an imaging exposure.

BRIEF DESCRIPTION OF THE FIGURES

The invention is now described in more detail in reference to some of its preferable embodiments and the attached drawings, of which.

DETAILED DESCRIPTION OF THE INVENTION

Figure 1:
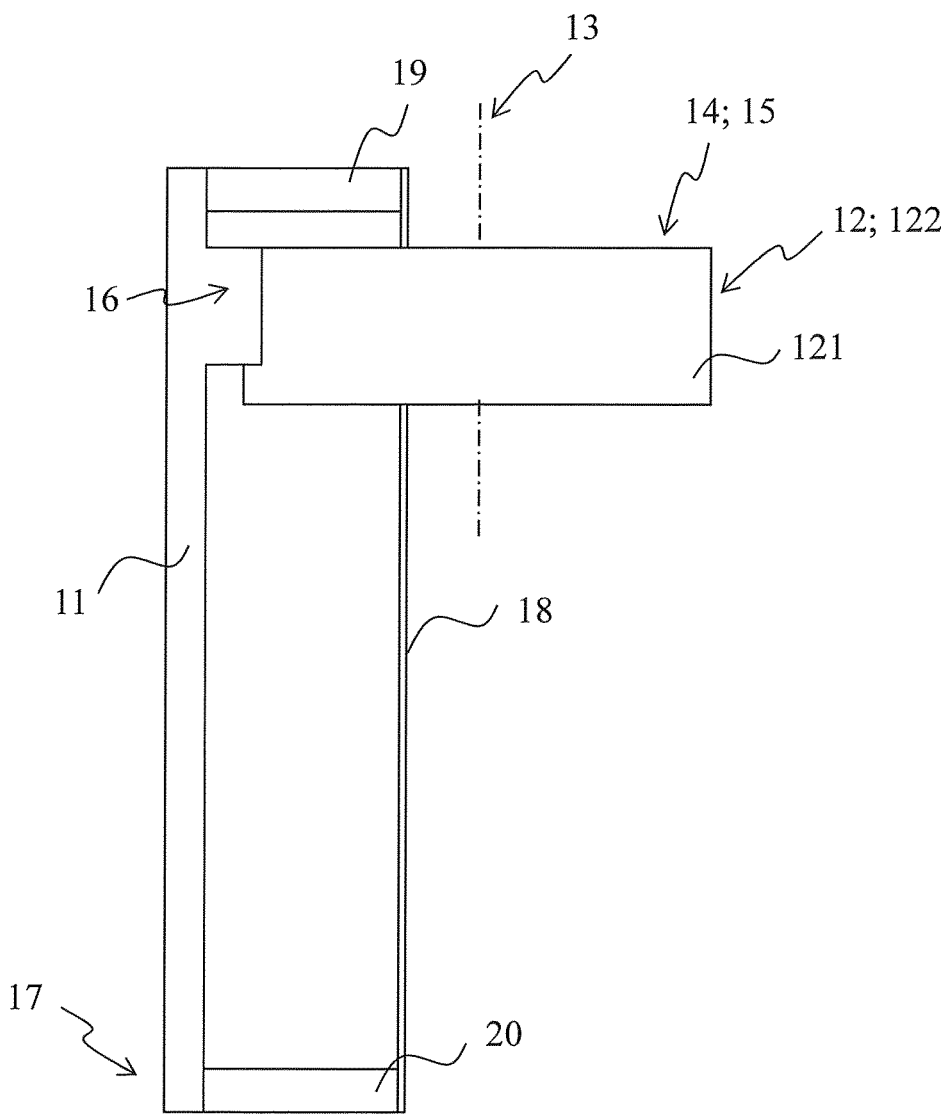
FIG. 1 is a schematic general side view showing components, as an example, of an imaging apparatus applicable to comprise features of the present disclosure.

A more complete understanding of components, processes and apparatuses disclosed herein can be obtained by reference to the accompanying drawings. These figures are merely schematic representations based on convenience and the ease of demonstrating the present disclosure and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings and are not intended to define or limit the scope of the disclosure. In the drawings and the following description below, it is to be understood that like numeric designations refer to components of like function.

The singular forms "a," "an," and "the" include plural referents unless the context clearly dictates otherwise.

Terms about, generally and substantially when used herein are intended to encompass structural or numerical modifications which do not significantly affect the purpose of the element or number modified by such term. For example, the term substantially may include a range of variance such as 25%, or 10%, or 0% from the stated relationship.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named elements/steps and permit the presence of other elements/steps.

FIG. 1 shows an apparatus comprising a longitudinally extending frame part 11 extending in a first direction and having a first end and a second end. From this longitudinally extending frame part 11, or "an elongated frame part 11", extends in a second direction a support construction 12 which supports an X-ray source 14 and an X-ray detector 15 (not as such visible in FIG. 1), the second direction being substantially orthogonal to the first direction. The X-ray source 14 and the X-ray detector 15, which together can be referred to as an X-ray imaging assembly 14, 15, or be part thereof, may be mounted to the support construction 12 for the X-ray source 14 and the X-ray detector 15 essentially opposite to each other yet in embodiments of the invention, their mutual position may also be arranged to be adjustable.

It is to be noted that the apparatus of FIG. 1, comprising structures as discussed above, is just an example of one preferable embodiment in the context of which the invention can be implemented. Just as an example, frame and support constructions of also other kind may be applicable, like those comprising "a C-shaped arm" for supporting the X-ray source and the X-ray detector.

While medical and dental X-ray imaging apparatus often include a patient support, FIG. 1 shows one specific kind patient support 18 structure mechanically connected to the elongated frame part 11. This patient support 18, applicable for use in various embodiments of the invention, comprises a surface which extends substantially in parallel with the elongated frame part 11. And while such patient support 18 is optional, in the particular embodiment of FIG. 1 the patient support 18 is essentially of the same length as the elongated frame part 11.

Examples on how the X-ray source 14 and the X-ray detector 15 may be mounted to the support construction 12 for the X-ray imaging assembly 14, 15 are presented when discussing some of the other Figs. of this disclosure further below while FIG. 1 shows, in general, the support construction 12 for the X-ray imaging assembly 14, 15 comprising a housing 121. The housing 121 may cover a ring-shaped gantry 122, to which the X-ray imaging assembly 14, 15 is mounted. In one embodiment, the housing 121 may extend to cover the X-ray source 14 and the X-ray detector 15 entirely, in another the gantry housing 121 may cover the construction by which the X-ray source 14 and the X-ray detector 15 are mounted to the gantry 122 while not the X-ray source 14 and the X-ray detector 15 themselves.

The X-ray source 14 and the X-ray detector 15 may be arranged to be rotatable about a rotation axis 13. In one embodiment, the ring-shaped gantry 122 to which the X-ray source 14 and the X-ray detector 15 are mounted is rotatable. In the particular construction shown in FIG. 1, showing the schematic general side view as discussed above, this rotation axis 13 coincides or can be made to coincide with the central axis of the support construction 12 for the X-ray imaging assembly 14, 15, of the housing 121 and of the ring-shaped gantry 122 as discussed above.

Thus, according to one aspect not directly visible in FIG. 1, for example, the apparatus comprises a driving mechanism 16 arranged to drive the X-ray source 14 and the X-ray detector 15 about a rotation axis 13. The rotation axis 13 may be a physical axis, or a virtual rotation axis as in the case of FIG. 1.

According to one aspect, for example, the rotation axis 13, or the center of rotation of the X-ray source 14 and the X-ray detector 15 when being driven along a curved path and thus defining a location of the virtual rotation axis 13, coincides with the central axis of the gantry 122.

According to one aspect, the rotation axis 13 is an instantaneous (optionally virtual) rotation axis and the location of the instantaneous rotation axis in relation to the central axis of the support construction 12 for the X-ray imaging assembly 14, 15, of the housing 121 and/or of the ring-shaped gantry 122 as discussed above can be arranged to be changed.

The rotation may be arranged to be performed by rotating the gantry 122 by any conventional mechanism known to those skilled in art. In one embodiment, a driving belt driven by at least one pulley is arranged to extend around a ring-shaped gantry 122. Such construction can enable implementing rotating the gantry 122 over an angle even exceeding 360 degrees.

According to another aspect, another driving mechanism 17 may be arranged to the apparatus to enable moving the support construction 12 for the X-ray imaging assembly 14, 15 back and forth in a direction which is substantially parallel with the direction in which the elongated frame part 11 extends. According to one aspect, the driving mechanism 17 may be arranged to move the support construction 12 along or alongside the elongated frame part 11.

According to one aspect, the driving mechanism 17 to drive the support construction 12 in a direction which is substantially parallel with the direction in which the elongated frame part 11 extends can comprise a motor arranged to the support construction 12 for the X-ray imaging assembly 14, 15 itself.

Regardless of the details of the construction of the driving mechanism 17 to drive the support construction 12 along or alongside the elongated frame part 11, in one embodiment the construction of the apparatus allows for driving the support construction 12 essentially the whole length between the first and second ends of the elongated frame part 11.

Figure 2A:
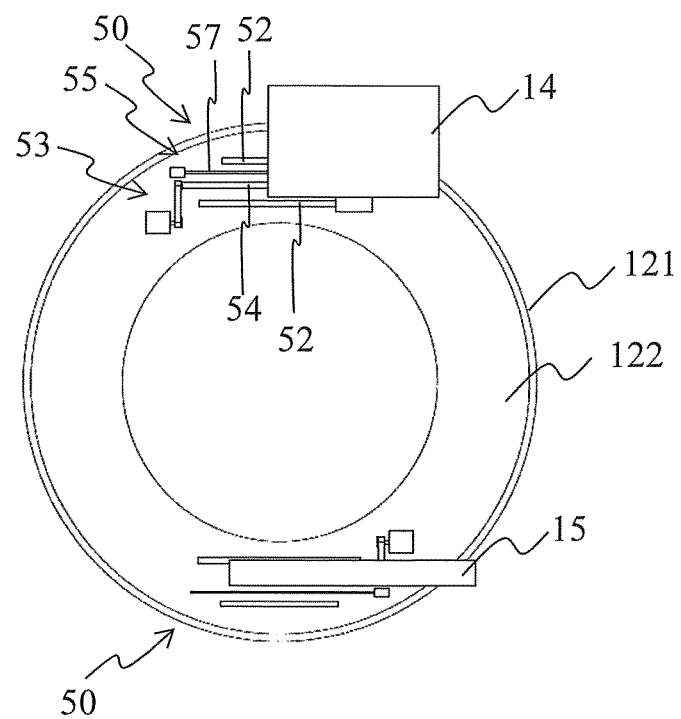
FIGS. 2a-2c show some structural details, as an example, of an embodiment comprising a motorized guiding construction arranged in functional connection with an X-ray source and an X-ray detector.
Figure 2B:
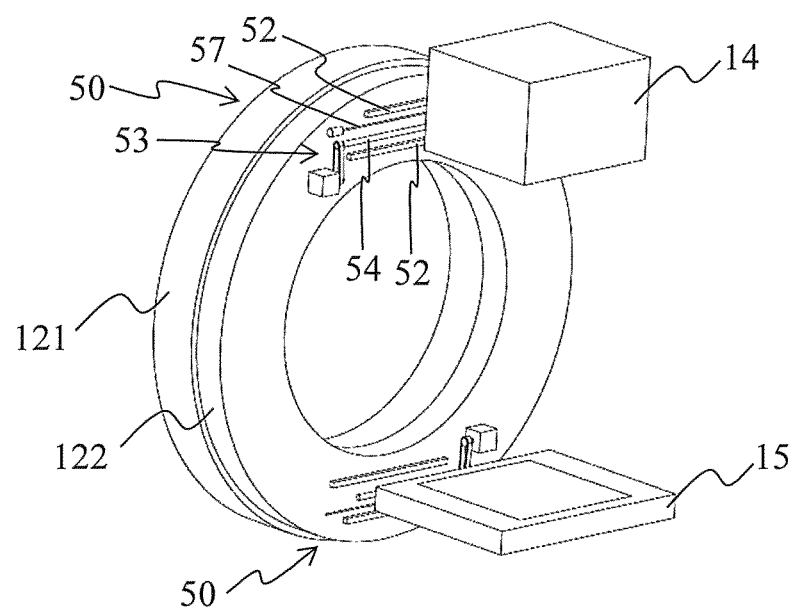
Figure 2C:
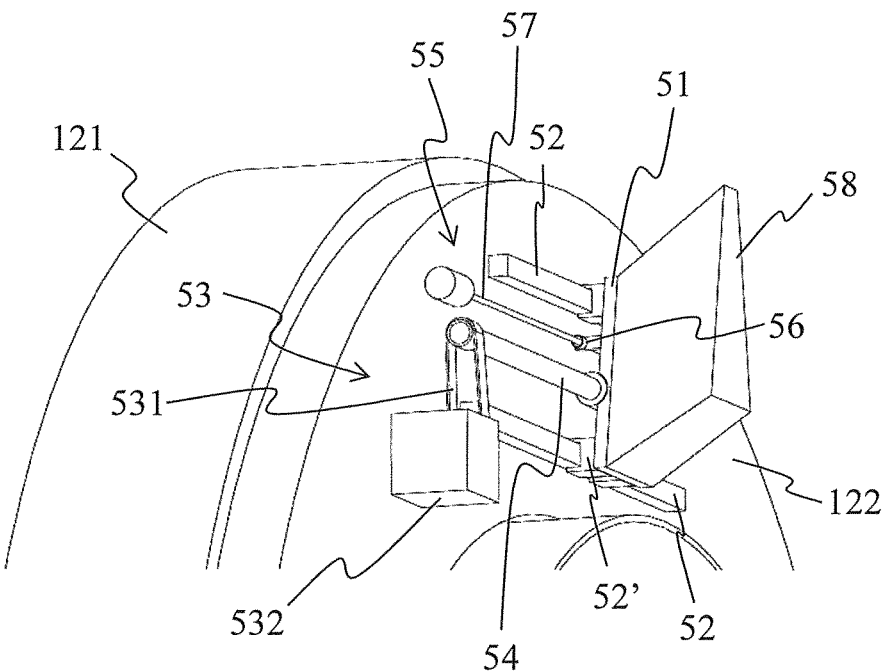

Turning to FIGS. 2a-2c they show, as an example, some structural details of one possible embodiment which can be used when implementing the invention. In FIGS. 2a-2c, a part of the housing 121 of the support construction 12 for the X-ray imaging assembly 14, 15 is removed, which makes visible a guiding construction 50 which can be arranged in functional connection with at least the X-ray source 14 of the imaging assembly 14, 15. According to one embodiment, the guiding construction 50 is motorized.

While FIGS. 2a-2c show two guiding constructions 50, which are configured to enable laterally moving the X-ray source 14 and the X-ray detector 15 in relation to their support construction 12, or in relation to the gantry 122, according to one embodiment only for the X-ray source 14 is arranged a guiding construction 50.

The lateral movement of the X-ray source 14 and/or the X-ray detector 15 in relation to the support construction 12, or the gantry 122, can be implemented to take place on a plane which is orthogonal to the rotation axis 13 about which the X-ray source 14 and the X-ray detector 15 are arranged to rotate.

According to one aspect, for example, the at least one guiding construction 50 as discussed herein is mounted to a ring-shaped gantry 122 arranged to the support construction 12 supporting the X-ray imaging assembly 14, 15.

The range of movement provided by the guiding construction 50 may comprise a base position and a first and a second extreme position, which locate in opposite directions from the base position.

While FIGS. 2a-2c show an embodiment in which structurally identical guiding constructions 50 are arranged for both the X-ray source 14 and the X-ray detector 15, and show the guiding construction 50 in different details, for clarity of the Figs. and since not all of the components are even visible in all of them, not each and every component is presented in each of the FIGS. 2a-2c with a related reference number.

According to one aspect, as an example, the guiding construction 50 comprising a carriage 51 (visible in FIG. 2c) mounted to at least the X-ray source 14 to enable lateral moving of it. A range of the lateral movement of the carriage 51 may include a base position and a first and a second extreme position locating in opposite directions from the base position.

Further, according to one aspect, the at least one guiding construction 50 comprises at least one guiding groove or rail 52 on the side of the support construction 12, or of the gantry 122, and a mating construction 52' on the side of the carriage 51 (again, visible in FIG. 2c).

According to one aspect, the at least one guiding construction 50 can comprise a motorized construction 53 in functional connection with the carriage 51, the motorized construction 53 providing the lateral moving of at least the X-ray source 14 within said range of lateral movement.

According to one aspect, the motorized construction 53 can comprise a driving screw 54 which is aligned parallel with the at least one guiding groove or rail 52 and arranged in functional connection with the carriage 51. According to the embodiment shown in FIGS. 2a-2c, the driving screw 54 is arranged to be rotated via a belt 531 driven by a motor 532 yet another construction to rotate the driving screw 54 may be used instead.

According to yet another aspect, the guiding construction 50 can include a position sensor arrangement 55 configured to acquire information relating to a position of the X-ray source 14 and/or the X-ray detector 15, within the range of the lateral movement of at least either of the X-ray source 14 and the X-ray detector 15.

According to one aspect, the position sensor arrangement 55 can be configured to detect a position of the carriage 51 within the range of the lateral movement of the carriage 51.

According to one further aspect, a signal path can be arranged between the at least one guiding construction 50 and the control system of the apparatus.

According to one aspect, the signal path can comprise a signal path between the position sensor arrangement 55 and the control system of the apparatus.

According to one aspect, the position sensor arrangement 55 is an absolute position sensor arrangement 55.

According to one aspect, the absolute position sensor arrangement 55 can comprise a magnetic component 56 structurally connected to the carriage 51 and movably connected to a rod 57 extending in parallel with the at least one guiding groove or rail 52 and the driving screw 54.

According to one aspect, the first longitudinally extending frame part 11 extends horizontally or is arranged to be moved so as to extend horizontally and the motorized construction 53 of the guiding construction 50 is arranged as self-holding regarding all i) positions of at least either of the X-ray source 14 and the X-ray detector 15 within the range of their lateral movement and ii) rotational positions at which the first driving mechanism 16 is configured to move the X-ray source 14 and the X-ray detector 15 about the virtual or physical rotation axis 13.

According to one embodiment, the X-ray source 14 and the X-ray detector 15 extend from one same side of the ring-shaped gantry housing 121, while that particular side of the ring-shaped gantry housing 121 can comprise an otherwise closed surface but on which surface there is an opening 59 for at least either of the X-ray source 14 and the X-ray detector 15. The opening 59 can be dimensioned to allow for the range of lateral movement of the X-ray source 14 and/or the X-ray detector 15 as guided by the at least one guiding construction 50.

Figure 3:
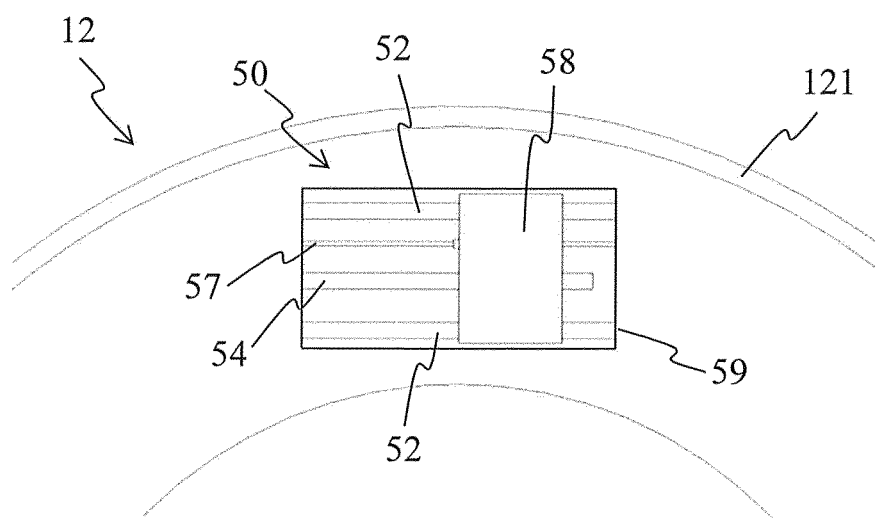
FIG. 3 shows a guiding construction as shown in FIGS. 2a-2c as partially covered by a housing of a support construction for the X-ray source 14 and the X-ray detector 15.

FIGS. 2c and 3 show an embodiment including a mounting bracket 58 configured to extend through the opening 59 in the gantry housing 121. The mounting bracket 58 can be fixed to the carriage 51 at one side and, to the X-ray source 14 and/or the X-ray detector 15 at the other. Differently dimensioned mounting brackets 58 can be used. As another detail, concerning the guiding construction in general, the movement in enables needs not necessarily to be lateral.

Figure 4A:
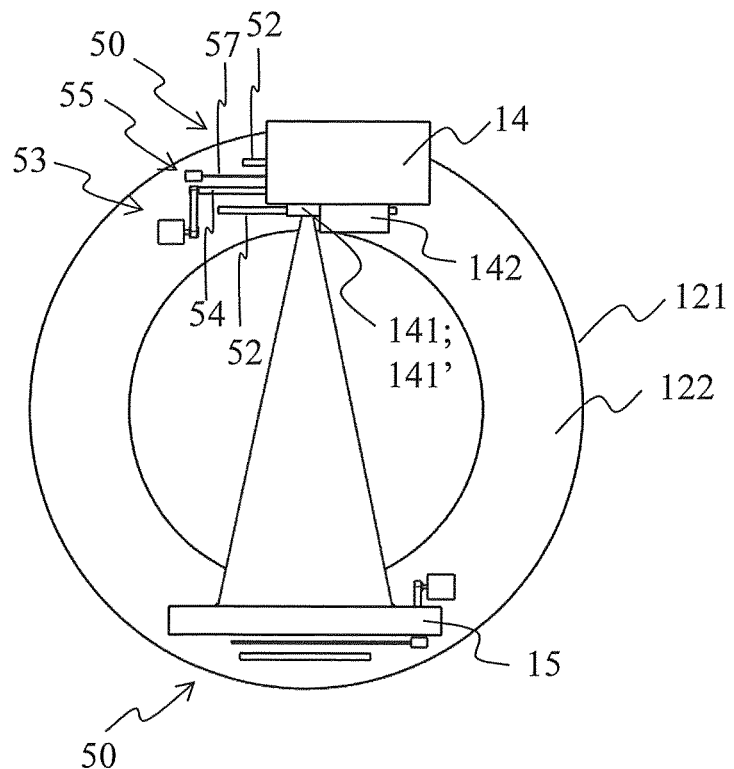
FIGS. 4a-4c show, as an example, a construction to realize a principle of projecting a visible light field pattern towards the X-ray detector from essentially the same location as from where an X-ray beam is configured to be emitted, during an exposure.
Figure 4B:
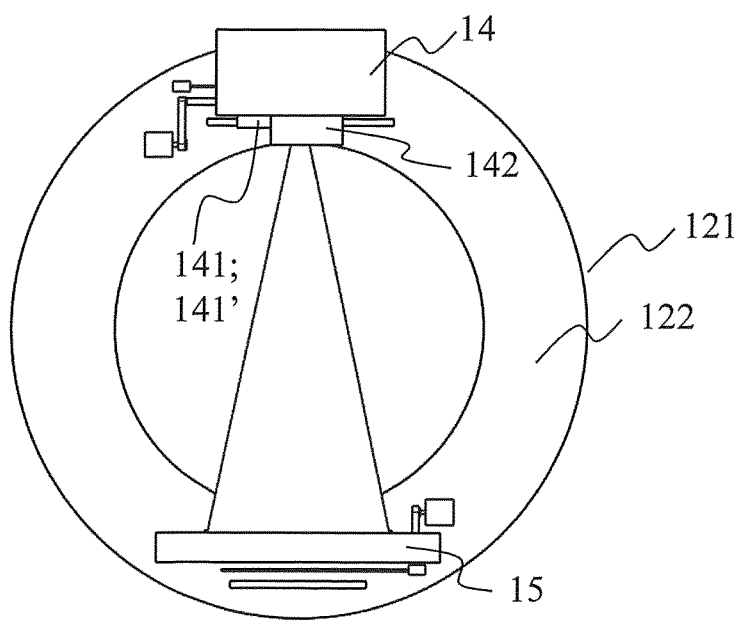
Figure 4C:
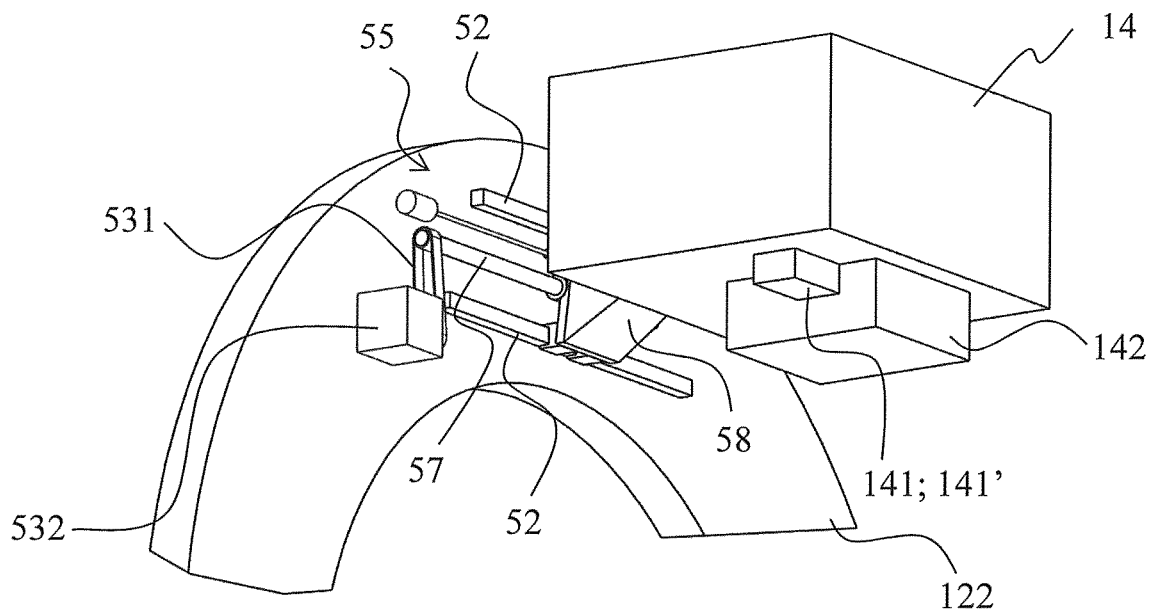

Referring to FIGS. 4a-4c, a configuration is shown which as compared to FIGS. 2a-2c further includes a light emitting component. Or, in reference to the disclosure of background to the invention above, shows a light field indicator 141 comprising a visible light emitting construction 141' configured to emit a visible light field pattern.

In the example construction of FIGS. 4a-4c, the visible light emitting construction 141' is arranged to locate as fixed to a collimator construction 142 of the X-ray source 14 and these three components are arranged movable together as a fixed assembly. Moving of that assembly can be realized, for example, by the kind of guiding construction 50 as discussed above.

The light emitting construction 141' may also, as an alternative, be directly attached to the (housing of the) X-ray source 14, or elsewhere to a frame structure of a collimator construction 142 attached to or being functionally connected to the X-ray source 14.

In a construction such as shown in FIGS. 4a-4c, the visible light emitting construction 141' can be configured to be capable of projecting different light field patterns as for their shape and size. Preferably, of essentially the same shapes and/or sizes to which the X-ray beam collimator construction 142 is configured to be able to limit an X-ray beam.

Thus, when considering using the construction, the arrangement as shown in FIGS. 4a-4c comprising the X-ray source 14, the collimator construction 142 and the visible light emitting construction 141' can be moved, prior to an imaging exposure, to a position according to FIG. 4a so that the visible light emitting construction 141' will locate essentially at the same location as where the X-ray source locates in FIG. 4b, i.e. at a position from which an X-ray beam will be emitted during an imaging exposure.

In other words and more generally, the support construction 12 carrying the X-ray source 14 and the X-ray detector 15 may be configured to enable positioning the X-ray source 14 and the visible light emitting construction 141' at essentially the same location, so as to when at a given time locating at said essentially same location, they may direct a given field pattern in essentially the same direction towards the X-ray detector 15.

Constructions like the one shown in FIGS. 4a-4c thus enable e.g. a procedure to first drive the visible light emitting construction 141' in the position according to FIG. 4a, position an anatomy to be imaged in the imaging area of the apparatus, and then adjust the light field pattern thus cast on the anatomy according to a given imaging mode to be applied, and according to that particular individual anatomy.

The procedure may further include the control system of the apparatus comprising information concerning correlation between dimensions of the light field pattern cast towards the X-ray detector 15 and collimation of the X-ray beam, so as to have dimensions of the visible light and X-ray irradiation beams substantially correspond to each other, at the proximity of the X-ray detector 15. Or, in other words, to have dimensions of the visible light pattern and the X-ray irradiation field pattern substantially correspond to each other at a given distance from the X-ray detector 15.

According to one embodiment, information of the size and shape of the visible light pattern is provided for the X-ray beam collimator control and a component or components of the collimator construction 142 are moved so as to delimit an opening by which the shape and size of the X-ray beam pattern hitting the anatomy will at least substantially correspond to that of the light pattern, when the X-ray source 14 has been moved to a location which substantially corresponds to the location at which the visible light pattern was projected on the anatomy.

According to another embodiment, adjusting the light field pattern takes place via controls of the collimator construction 142 such that when the opening the collimator construction 142 limits is adjusted, the shape and size of the light field pattern gets adjusted accordingly, as based on correlation information recorded in the control system of the apparatus. That is, in such embodiment, no separate input means for adjusting the light field pattern is needed as control thereof may take place via controls of the collimator construction 142.

In both embodiments above, the control system of the apparatus may comprise information on which kind of an X-ray beam and light field pattern correspond to each other under given circumstances, like in a context of a given imaging mode to be applied. The imaging mode may be, for example, imaging a certain anatomy from a certain direction which means that, generally speaking, the surface of the anatomy will locate at more or less the same distance from the X-ray detector 15—and thus also more or less the same distance from the X-ray source 14 and the light emitting component 141 when being positioned at that same location in the support construction 12. When an imaging mode includes rotation about an anatomy, i.e. scanning the anatomy by an X-ray beam, the light field pattern may be configured to show, instead of or in addition to showing location of the X-ray beam pattern at the initial position of the X-ray beam, the entire or at least part of the entire area where the X-ray beam will travel during the scan. In case of a tomography and especially a CBCT imaging mode, the area of an anatomy indicated by the visible light emitting component 141' may relate to the volume of the anatomy which a given CT imaging mode, in case using a given coolimation setting of the X-ray beam, will cover.

Using the kind of arrangement shown in FIGS. 4a-4c, for example, depending on the context it is not necessarily essential to have the light field pattern and the X-ray beam pattern of precisely the same shape and size. For one, the focus or emission points of the diverging visible light and X-ray beams need not to locate at exactly the same distance from the X-ray detector 15, and their diverging angles need not to be exactly the same. Regarding differences there may be, they can be taken into account when knowing the differences, and the distance to the location (i.e. surface of an anatomy) at which the patterns should essential match. Such correlation information can be recorded in the control system of the apparatus and thus the pattern dimensions be configured to essentially correspond to each other under given circumstances.

While FIGS. 4a-4c show an embodiment in which the components X-ray source 14, X-ray beam collimator construction 142 and visible light emitting construction 141' are arranged to be moved as an integrated assembly, which embodiment includes configuring the control system of the apparatus to provide for the X-ray beam collimator construction 142 the information of the size and shape of the light field pattern being generated, or vice versa, an alternative arrangement is to realize only the X-ray source 14 and the light field indicator 141 as a fixed assembly, which would then be arranged to be moved in relation to the collimator construction 142. In such embodiment, the collimator construction 142 could be used to limit both the visible light beam and the X-ray beam.

As to the accuracy of correspondence of the beam sizes and shapes, or the field pattern sizes and shapes, it is in view of certain aspects more critical to get them closely match each other in the context of using the imaging apparatus to take a single 2D radiograph, as compared to 3D tomographic imaging.

Figure 5:
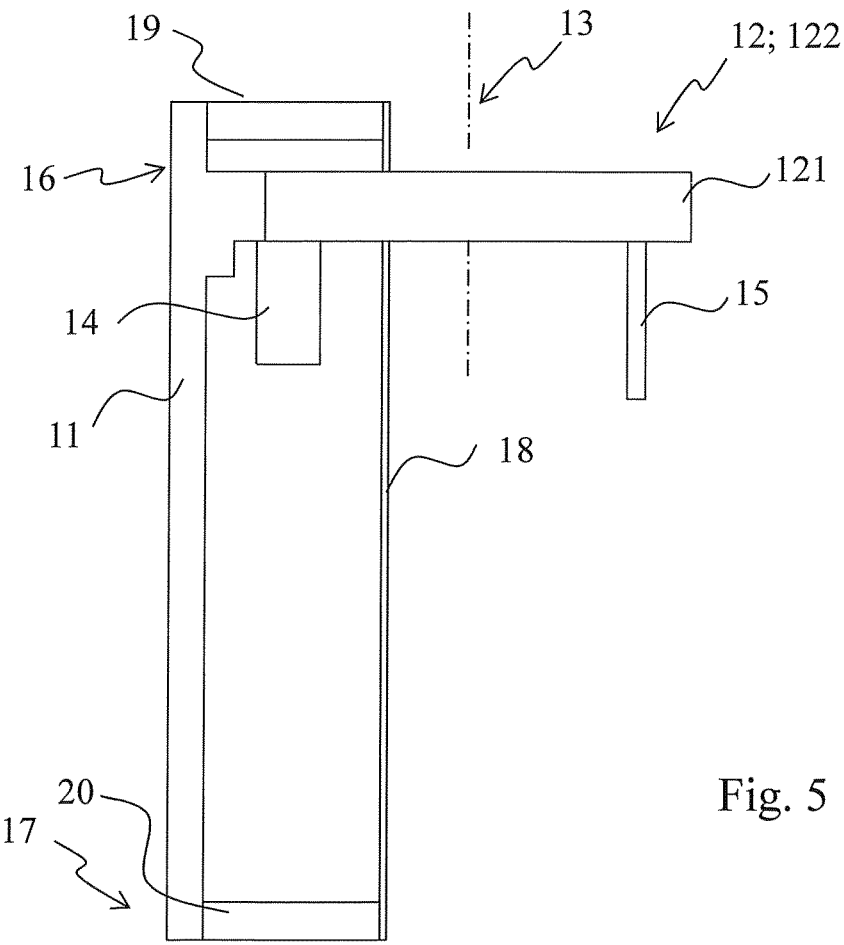
FIG. 5 shows an embodiment in which the X-ray source and the X-ray detector are located and extend outside the housing of the support construction for the X-ray source and the X-ray detector.

In reference to FIG. 5, according to one aspect, the support construction 12 comprises a ring-shaped gantry housing 121 which houses i) at least one guiding construction 50 and optionally also ii) driving mechanism 16 arranged to move the X-ray imaging assembly 14, 15 about the virtual or physical rotation axis 13, whereas the X-ray source 14 and the image detector 15 are arranged to locate or extend outside the ring-shaped gantry housing 121.

According to one embodiment, the X-ray source 14 and/or the X-ray detector 15 can include a housing for the X-ray source 14 and/or the X-ray detector 15 which is so designed and dimensioned that in all positions within the range of the lateral movement of at least either of the X-ray source 14 and the X-ray detector 15, the housing covers the opening 59 through which the mounting bracket 58 extends.

According to one aspect, in case of there being more than one guising construction 50 they can comprise the same number of components having the same functions so as to form similarly functioning assemblies. As an example, the guiding constructions may be identical while optionally the mounting brackets 58 may be different, as adapted specifically for the X-ray source 14 and the image detector 15.

According to one aspect when the housing 121 of the support construction 12 does not encase the X-ray source 14 and the X-ray detector 15, but functions primarily or solely as a housing for e.g. the ring-shaped gantry 122, to which the X-ray source 14 and the X-ray detector 15 are mounted, and for the structures arranged to the apparatus to drive the X-ray source 14 and the X-ray detector 15 about the rotation axis 13, the support construction 12 can be realized to be lighter and to provide a possibility for better access for patients and personnel to the imaging volume between the X-ray source 14 and the X-ray detector 15.

Such embodiment can also make it easier for the personnel to have a clear line of sight at the imaging volume inside the housing 121, whereto the patient is to be positioned for an exposure.

Figure 6:
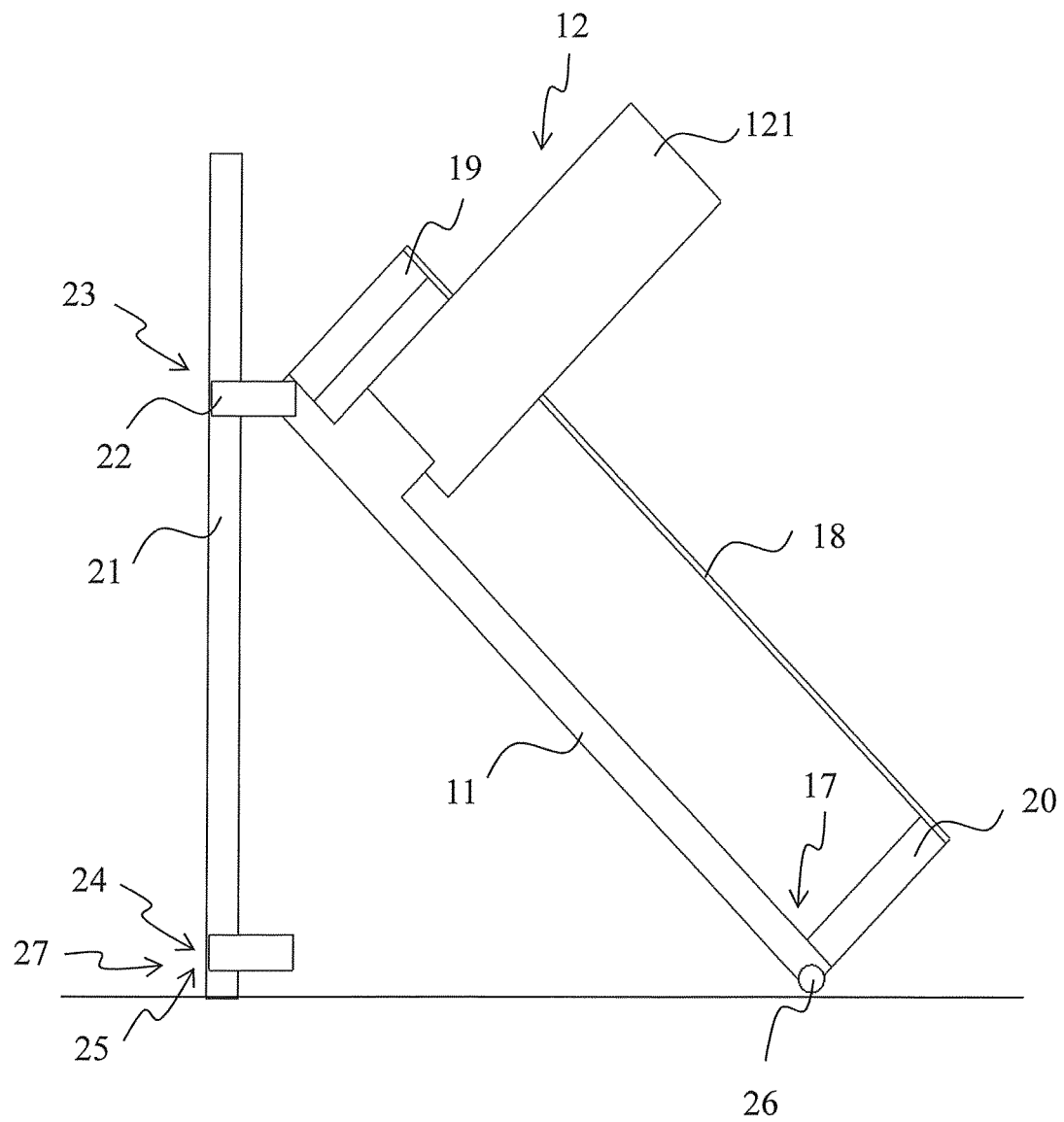
FIG. 6 shows a schematic general side view of an embodiment like the one shown in FIG. 1, arranged with elements enabling changing orientation.

Turning to FIG. 6 which shows, as an example and as a schematic general side view, certain components of an embodiment in which, in addition to what can be referred to as a first elongated frame part 11 discussed above, there is a second elongated frame part 21 mechanically connected to the first elongated frame part 11, of essentially the same length as the first elongated frame part 11.

According to one aspect and still referring to FIG. 6, at the proximity of the first end of the elongated frame parts 11, 12 is arranged an articulated connection construction 22 to mechanically connect the first and second elongated frame parts 11, 21, to allow for tilting of the first elongated frame part 11 about at least one tilt axis in relation to the second elongated frame part 21. The at least one tilt axis may be an axis which is orthogonal to the direction in which the first and second elongated frame parts 11, 21 extend as well as to direction in which the support construction 12 for the X-ray imaging assembly 14, 15 extends—perpendicularly from the first longitudinally extending frame part 11.

In the embodiments shown in FIG. 6, the at least one tilt axis is horizontal.

According to another aspect, on the side of the second elongated frame part 21, a mounting structure 23 not directly visible in FIG. 6 is arranged in connection with the articulated connection construction 22. The mounting structure 23 is arranged movable along or alongside the second elongated frame part 21.

According to another aspect, for example, in the proximity of the second end of the second elongated frame part 21 is arranged a locking mechanism 24 configured to enable connecting and disconnecting the first and second elongated frame parts 11, 21. Particularly, the locking mechanism 24 may be arranged in the proximity of the second end of the first and second elongated frame parts 11, 21 and as configured to enable connecting together and disconnecting the first and second elongated frame parts 11, 21 at the proximity of the second ends of the first and second elongated frame parts 11, 21.

When the second elongated frame part 21 is mounted stable and the locking mechanism 24 is not connecting the first and second elongated frame parts 11, 21, the second end of the first elongated frame part 11 is free to move laterally while the articulated connection 22 between the frame parts 11, 21 allows for turning of the first elongated frame part 11 about the horizontal tilt axis, at the proximity of the first end of the first elongated frame part 11. In case of a vertical starting position, such movably arranged mounting structure as discussed above allows for descending and ascending of the first end of the first elongated frame part 11.

While the construction allowing for tilting of the first elongated frame part 11 and descending and ascending of the first end of the first elongated frame part 11, as well as that of the locking mechanism 24 discussed above may vary, examples of such are disclosed in more detail in a co-pending patent application FI 20190054, which is incorporated herein by reference.

FIG. 6 shows the apparatus at a stage where the first end of the first elongated frame part 11 has moved downwards and the second end of the first elongated frame part 11 has moved horizontally on a surface. The apparatus of FIG. 6 may be configured to allow for descending of the first end of the first elongated frame part 11 all the way to the proximity of the second end of the second elongated frame part 21.

According to yet another aspect, not directly visible in FIG. 6, in functional connection with the second elongated frame part 21 is arranged a driving mechanism 27 to drive the mounting structure 23 along or alongside the second elongated frame part 21. When being in mechanical connection with the first elongated frame part 11, at the proximity of the first end of it, the driving mechanism 27 can move the first end of the first elongated frame part 11 in a direction in which the second elongated frame part 21 extends.

The driving mechanism 27 to drive the mounting structure 23 may be a construction similar with the driving mechanism 17 driving the support construction 12 of the X-ray imaging assembly 14, 15 along or alongside the first elongated frame part 11.

According to one aspect, the driving mechanism 27 to drive the mounting structure 23 comprises a chain drive.

Figure 7:
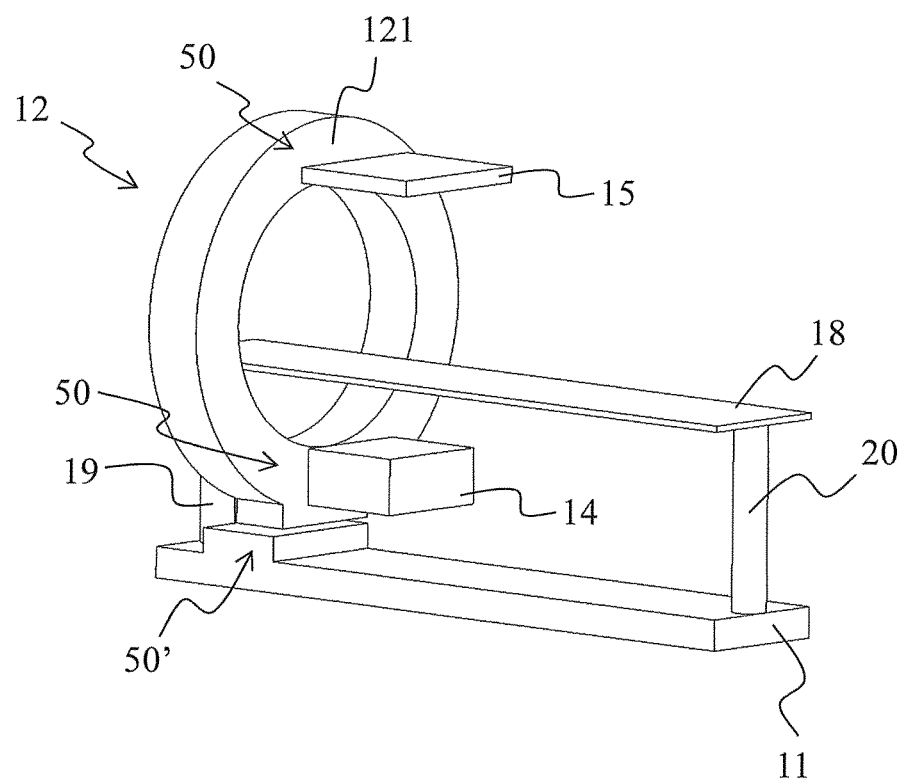
FIG. 7 is a schematic general presentation of an apparatus in horizontal position with certain components thereof driven to locations other than their base positions.

FIG. 7 is a schematic general presentation of an apparatus, as an example, extending in horizontal direction. While not shown in FIG. 7, the apparatus may comprise constructions as discussed in connection with FIG. 6 which allows for changing the direction in which the elongated frame part 11 extends. The support construction 12 for the X-ray imaging assembly 14, 15 in FIG. 7 is not similar with that of FIG. 6, while FIG. 7 shows certain components of the apparatus as driven to locations other than their base position.

That is, regarding e.g. the aspect of access to the volume between the X-ray source 14 and the X-ray detector 15, FIG. 7 illustrates how certain components of the apparatus may be moved to various locations within ranges of movements arranged for them. According to that embodiment, while the embodiments discussed above to laterally move at least either of the X-ray source 14 and the X-ray detector 15 can be used to ease access of a patient inside the support construction 12 for the X-ray imaging assembly 14, 15, another similarly construed construction or another similarly functioning construction may be arranged in the apparatus to also laterally move the support construction 12 for the X-ray imaging assembly 14, 15 itself, in relation to the elongated frame part 11. By incorporating such linear movement mechanism 50' to the apparatus, e.g. even more room may be provided for the patient to enter the imaging area and then get properly positioned for an exposure.

Thus, according to one aspect, the apparatus further comprises a linear movement mechanism 50' arranged to enable moving the support construction 12 for the X-ray imaging assembly in relation to the longitudinally extending frame part 11 in a direction which is at right angles to the direction in which the longitudinally extending frame part 11 extends. A range of the linear movement of the support construction 12 may comprise a base position in relation to the first longitudinally extending frame part 11 and a first and a second extreme position.

When the support construction 12 for the X-ray imaging assembly 14, 15 extends in a direction at right angles to the longitudinally extending frame part 11, the direction in which the linear movement mechanism 50' moves the support construction 12 for the X-ray imaging assembly 14, 15 in relation to the longitudinally extending frame part 11 is also at right angles to that direction.

Concerning the base position provided by the linear movement mechanism 50' for the support construction 12 for the X-ray imaging assembly 14, 15, in embodiments either of the first and second extreme positions may be the base position. The same applies concerning the guiding construction 50 for at least the X-ray source.

Figure 8A:
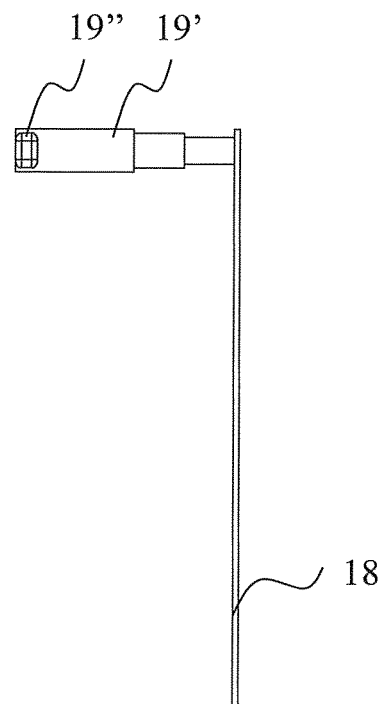
FIG. 8a shows, as an example, some details of a patient support suitable for use in an apparatus of the present disclosure.

According to yet another aspect and as shown in FIG. 8a, the connection construction 19, 20 which mechanically connects the patient support 18 to the elongated frame part 11 may comprise a patient support adjustment mechanism 19', 20' configured to enable displacing the patient support 18 closer and further away from the (first) elongated frame part 11.

According to another aspect, a patient support driving mechanis 20" is arranged in functional connection with the patient support adjustment mechanism 19', 20'.

According to another aspect, the patient support adjustment mechanism 19', 20' may comprise a first adjustment mechanism 19' arranged together with its driving mechanism 19" comprised in the patient support driving mechanism 19"', 20" substantially at the first end of the elongated frame part 11, and a second adjustment mechanism 20' arranged together with its driving mechanism 20" comprised in the patient support driving mechanism 19"', 20" substantially at the second end of the elongated frame part 11.

According to one aspect, for example, the patient support adjustment mechanisms 19', 20' is arranged in functional connection with the control system of the apparatus and the control system is configured to control the patient support driving mechanism 19"', 20" of the patient support adjustment mechanism 19', 20'.

According to one aspect, for example, the control system is configured to control the connection construction 19, 20 comprising the first adjustment mechanism 19' with its driving mechanism 19", arranged substantially at the first end of the (first) elongated frame part 11, and the second adjustment mechanism 20' with its driving mechanism 20", arranged substantially at the second end of the (first) elongated frame part 11, to keep at the first and second ends of the elongated frame part 11 an identical distance between the (first) elongated frame part 11 and the patient support 18 when adjusting the distance between the two.

According to another aspect, the distance between the ends of the (first) elongated frame part 11 and the patient support 18 can be adjusted to be different.

Figure 8B:
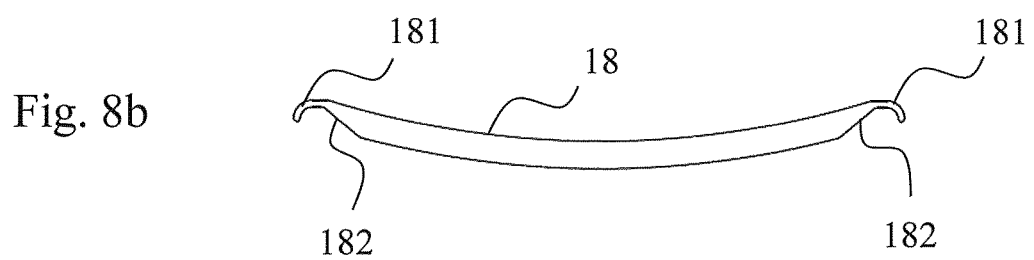
FIG. 8b shows, as an example, a cross section of a patient support.

According to one aspect, as shown in FIG. 8b, considering the above-discussed first direction of the patient support 18, its cross section as for its prevailing part is curved so as to better support a patient against the concave surface of the patient support 18.

According to one other aspect, as shown in FIG. 8b, at the edges 181 of that cross section of the patient support 18, the shape of the cross section turns into being curved in the opposite direction.

According to one other aspect and as further shown in FIG. 8b, near the edges of the above-discussed cross section of the patient support 18 and on the side opposite to the for its prevailing part concave surface, is arranged a holding structure 182. The holding structure 182 may be e.g. an elongated handle or an attachment structure to receive a strap designed to extent on or over the concave side of the patient support 18, to be used to provide further support to the patient and thus to help keeping still during an imaging exposure.

According to one aspect, and as already generally mentioned above, the various degrees of freedoms of movement of the components of apparatus, including those that may be arranged for the patient support 18, may be taken advantage of when positioning a patient, or to be more exact, an anatomy for an exposure. As an example, considering a situation of a patient's shoulder to be examined while lying on a patient support 18 like the one discussed above, one can first drive the patient support 18 to be located at a height position which is easiest for the patient to get on the patient support 18. Then, when the patient is lying on the patient support 18, at least one of i) the height position of the patient support 18, ii) horizontal position of the support construction 12 for the X-ray imaging assembly 14, 15, and iii) position of at least either of the X-ray source 14 and the X-ray detector 15 within the range of the lateral movement provided therefor can be adjusted so that the desired anatomy will locate at the field of view of the apparatus. This, obviously, within the limits of the degrees of freedoms of movement of the components of apparatus arranged therefor.

Structures according to embodiments enable arranging to the apparatus various patient entry and positioning operations. They can also be taken advantage of to perform e.g. other than traditional kind CT imaging and, in addition to CT imaging, also imaging modes with no rotation but mere linear movement of the X-ray imaging assembly may be deployed. Specifically, embodiments may be applied in the context of positioning an anatomy for an individual 2D imaging exposure.

The operation modes such as those discussed above may include, as a pre-exposure operation, driving the guiding construction 50 for the X-ray source 14 to which is connected the visible light emitting construction 141' such that the visible light emitting construction 141' will be moved to locate at essentially the base position of the X-ray source 14, and adjusting the field pattern generated by the visible light emitting construction 141' to be of a default shape and size. The default shape and size may be set according to an imaging mode, which may be arranged to be selected from the user interface of the apparatus.

According to an embodiment, a selected imaging mode may include driving the X-ray source 14 and the X-ray detector 15 a distance from their base positions. The apparatus may be configured to allow for, after such pre-exposure operation, to adjust the light field pattern, and thus the X-ray beam size and/or shape to be used during the imaging exposure, according characteristics of a given anatomy positioned for imaging.

In an embodiment, the arrangement is equipped with a component or components adapted to determine the location and/or the shape of the anatomy positioned for imaging, and the control system to then adjust the X-ray beam collimation and/or the projected visible light pattern on the anatomy using that knowledge. Technologies to determine distance to and shape of a surface in a coordinate system exist, as well as to transfer information from one coordinate system to another—in this case, when knowing the geometry of the (relevant components of the) imaging arrangement, and correlation of that to the coordinate system in which the surface location and shape is determined. In embodiments, instead of determining the shape of the surface of the anatomy, e.g. just a shortest distance from the said same location to the surface of the anatomy may be determined.

Pre-exposure operations relating to mutual positioning of the anatomy and the imaging assembly and adjusting the X-ray beam size and shape according to a given imaging mode, and even according to the anatomy to be imaged, may be applied in the context of various imaging modes arranged to the imaging apparatus. Such an operation may include, in general, the control system of the apparatus comprising geometric information regarding mutual positions of the X-ray source, the light emitting construction 141', the X-ray detector and/or the patient support such that for a given light field pattern and the location from where it is cast, the control system comprises corresponding collimation information for limiting the X-ray beam when the X-ray beam is emitted at a given location of the X-ray source, in a context of a given imaging mode.

An operation mode may include, as an example, a pre-exposure operation of—prior to optionally driving the X-ray source 14 and the X-ray detector 15 from their base positions, driving the guiding construction 50 for the X-ray source 14 to which is connected the visible light emitting construction 141' such that the visible light emitting construction 141' will be moved to locate at essentially the base position of the X-ray source 14, and adjusting the field light pattern generated by the visible light emitting construction 141' to be of a default shape and size. The default shape and size may be pre-set according to an imaging mode selected from the user interface of the apparatus.

According to an embodiment, as an example, the selected imaging mode includes driving the X-ray source 14 and the X-ray detector 15 a distance from their base positions. The apparatus may be configured to allow for, after such pre-exposure operation, adjusting the light field pattern, and thus the X-ray beam size and shape to be used during the imaging exposure, according characteristics of a given individual anatomy positioned for imaging.

Concerning a given patient entry operation or patient entry mode, according to one aspect, it includes the visible light emitting construction 141' being positioned at the same place as where the X-ray source will be positioned during, or at the beginning of a subsequent imaging exposure.

According to one aspect, then, the light field indicator 141 may be configured to be able to project a light beam of the same shape as is the shape of an X-ray beam the X-ray source 14 is configured to emit, or can be adjusted to emit. Such light field indicator 141 may be mounted to the same guiding construction 50 as the X-ray source 14, e.g. as a component separate from the X-ray source 14, so as to be movably mounted in relation to the support construction 12. The range of movement of the guiding construction 50 to which the X-ray source 12 and the light emitting component may be mounted is then preferably so configured that the X-ray source 14 and the light emitting construction 141' can be positioned at the same location within the range of movement the guiding construction 50 provides. Such configuration provides a novel apparatus by which one is able to cast a positioning light pattern on the object to be imaged from the same location at which the actual X-ray imaging exposure is to take place, or begin.

Figure 9:
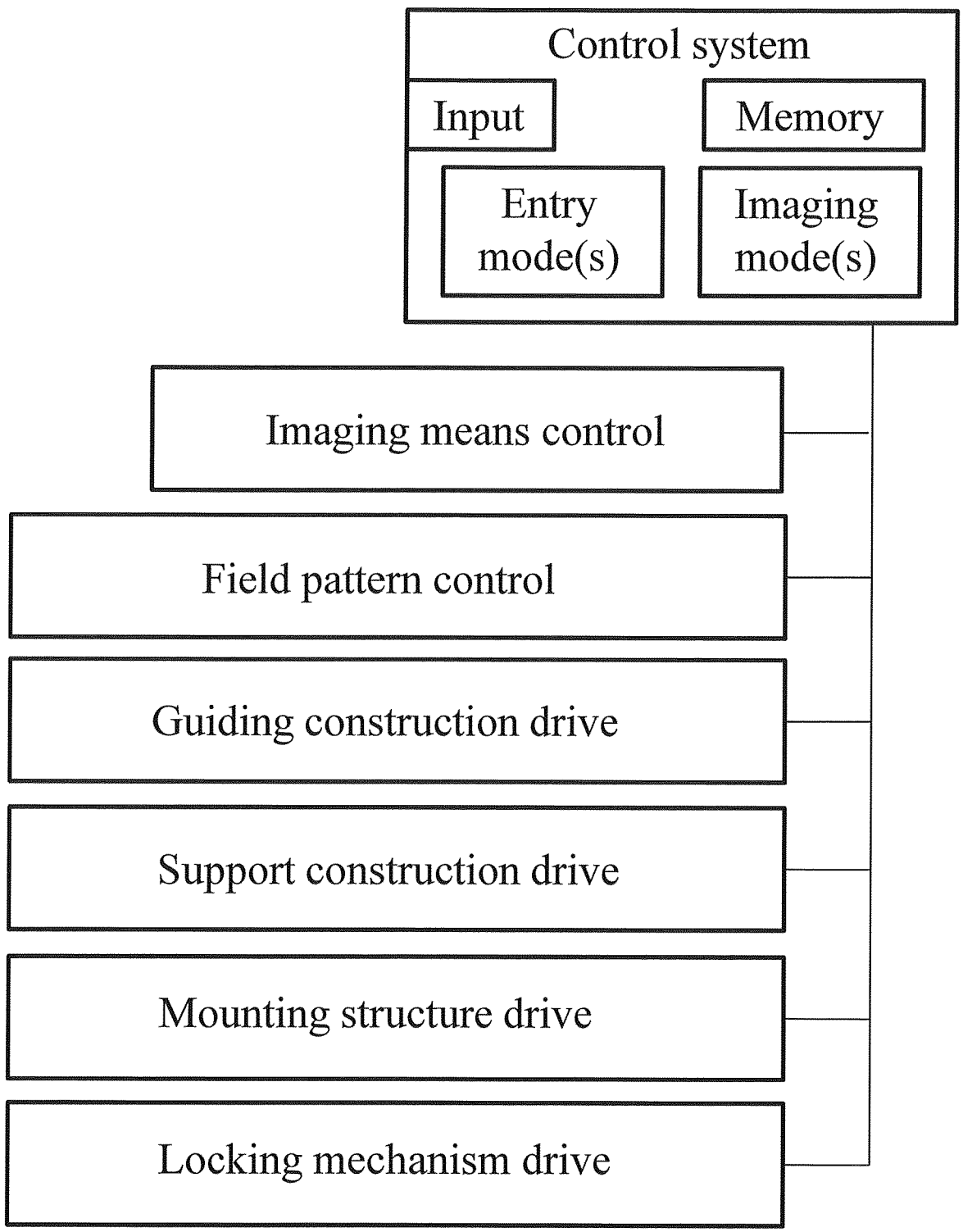
FIG. 9 is a block diagram showing an example of features of a control system of the apparatus.

FIG. 9 shows as a block diagram an example of components of a control system applicable for use in the apparatus. The control system according to FIG. 9 is configured to enable controlling, first of all, operation of the X-ray source 14 and the X-ray detector 15 (imaging means, or assembly) during an exposure, according to an imaging mode. Components controlling operation of the X-ray source 14 and the X-ray detector 15 can include components physically arranged to the X-ray source 14 and/or the X-ray detector 15 and/or elsewhere in the apparatus.

The control system may further be configured to control various driving means of the apparatus, such as those driving the one or more than one guiding construction 50 as well those moving the support construction 20 for the X-ray imaging assembly 14, 15. A signal path can also be arranged for controlling components discussed above relating to adjusting the shape and size of the field patterns, and positioning of those components in relation to the support construction 12.

The control system of FIG. 9 further shows optional features of rotating the X-ray imaging assembly 14, 15 as well as the patient entry mode feature, which may include controlling at least one of the above-discussed driving means.

Further shown in FIG. 9 is a signal path to the mounting structure 23 as discussed further above and, in case of the apparatus comprising a motorized locking mechanism 24 to connect and disconnect the first and second elongated frame parts 11, 21 as discussed above, the control system may also control driving of the locking mechanism 24.

Overall, the control system may be arranged to control the above-discussed operations or a portion thereof. The structures and functionalities discussed above offer various possibilities to ease positioning and performing imaging of a desired volume of a patient.

Control signals for various operations may be triggered as a response to a detected operation or input from the user interface of the apparatus. The memory of the control system may include various correlation information of pattern shapes and dimensions as discussed above, and related control protocols as discussed above, as well as protocols relating to one or more entry and/or imaging mode.

While various embodiments are discussed above, an apparatus of this disclosure can be described as a dental or medical X-ray imaging apparatus which comprises an X-ray detector, an X-ray source configured to generate X-ray irradiation and comprising a collimator construction functionally connected to the X-ray source, the collimator construction being configured to limit the X-ray irradiation generated by the X-ray source into a beam to be aimed in the direction of the X-ray detector and defining an X-ray irradiation field pattern, a light field indicator tor comprising a visible light emitting construction and being configured to project a visible light field pattern to be aimed in the direction of the X-ray detector, and a control system comprising control information relating to an imaging mode. The apparatus further comprises a support construction to which the X-ray source, the X-ray detector and the visible light emitting construction are mounted, while the support construction is configured to enable positioning the X-ray source and the visible light emitting construction at essentially the same location in relation to the support construction, so as to when at a given time locating at said essentially same location to direct a given field pattern in essentially the same direction towards the X-ray detector. Further, the apparatus may comprise a first frame part extending in a first direction and comprising a first end and a second end and wherein the support construction to which the X-ray source, the X-ray detector and the visible light emitting construction are mounted extends from the first frame part in a second direction essentially at right angles to the first direction.

To add to, or summarize some of the features discussed above, embodiments may include that the support construction may comprise a ring-shaped structure, which may comprise a ring-shaped gantry and a housing which houses at least the ring-shaped gantry.

Positioning of the X-ray source and the visible light emitting construction at essentially the same location may include arranging the X-ray source and the visible light emitting construction movable in a direction at right angles to both the first and second direction.

The X-ray source, the collimator construction and the visible light emitting construction are arranged to be movable as a fixed assembly.

On the other hand, the X-ray source and the visible light emitting construction may be arranged to be movable as a fixed unit in relation to the collimator construction.

The light field indicator may be configured to generate the visible light field pattern such that the pattern is a substantially evenly illuminated area or comprises a pattern of light fields which as a combination indicates an area. Further, the light field indicator may be configured to enable projecting visible light field patterns of different sizes and/or different shapes, and the collimator construction to enable limiting X-ray irradiation field patterns of different sizes and/or of different shapes.

The control system may comprise correlation information relating to dimensions of the visible light field pattern and the X-ray irradiation field pattern, at a given distance from the X-ray detector, and the light field indicator and the collimator construction be configured to enable adjusting dimensions and/or shape of their respective field patterns according to the correlation information such that the field patterns cover essentially the same area at said given distance from the X-ray detector. Further, or alternatively, the correlation information may include correlation information relating to a given imaging mode.

A given imaging mode may be a CBCT imaging mode and the control system be configured to enable indicating by the visible light field pattern an area at a given distance from the X-ray detector 15 relating to a volume which, regarding a given CBCT imaging mode and in case using a given collimation setting of the X-ray beam, will cover.

The arrangement may comprise a component or components configured to determine location and/or shape of an anatomy positioned for imaging, and the control system then configured to be able adjust the X-ray beam collimation and/or the projected visible light pattern on the anatomy using that knowledge, the location and/or shape then defining that given distance from the X-ray detector 15.

The control system may also be configured to receive information from the light field indicator on the characteristics of the visible light pattern it projects and to convert said received information to information on how to control operation of the collimator construction so as to adjust the X-ray irradiation field pattern to at least substantially correspond to the size and shape of the area the projected visible light pattern indicates.

The control system may further be configured to receive information from the collimator construction on the characteristics of the X-ray irradiation field pattern it limits and to convert said received information to information on how to control operation of the light field indicator so as to adjust the visible light field pattern to at least substantially correspond to the size and shape of the X-ray irradiation field pattern.

The apparatus may comprise a first guiding construction mounted to the support construction, and the X-ray source and the visible light emitting construction be mounted together as a fixed unit and the first guiding construction configured to enable moving said fixed unit, a range of said movement comprising a base position and a first and a second extreme position. The first guiding construction may comprise a carriage mounted to said fixed unit comprising the X-ray source and the visible light emitting construction, a range of said movement of the carriage comprising a base position and a first and a second extreme position.

The first guiding construction may comprise a at least one guiding groove or rail on a side of the support construction and a mating construction on a side of the carriage. On the other hand, the first guiding construction may comprise a motorized construction in functional connection with the carriage, the motorized construction providing the moving of the fixed unit comprising the X-ray source and the visible light emitting construction within that range comprising the first and second extreme positions. The first guiding construction may also include a position sensor arrangement configured to acquire information relating to a position of the fixed unit comprising the X-ray source and the visible light emitting construction within that range of movement, the position sensor arrangement being configured to detect a position of the carriage within the range of movement of the carriage. The first guiding construction may be configured to enable laterally moving said fixed unit and the motorized construction may comprise a driving screw, the driving screw being aligned parallel with the at least one guiding groove or rail and arranged in functional connection with the carriage.

The position sensor arrangement may comprise a magnetic component structurally connected to the carriage and movably connected to a rod extending in parallel with said at least one guiding groove or rail and said driving screw of the guiding construction.

A mounting bracket may be fixed to the carriage and, on the other hand, to the fixed unit comprising the X-ray source and the visible light emitting construction, to mechanically connect said fixed unit to the guiding construction.

A signal path can be provided between the first guiding construction and the control system. The signal path may comprise a signal path between the position sensor arrangement and the control system.

A signal path may also be provided between the collimator construction 142 and the control system, and between the light field indicator 141 and the control system, to enable controlling the collimator construction 142 and the light field indicator 141 according to the correlation information.

The ring-shaped structure may comprise a ring-shaped gantry which also houses the first guiding construction. The housing may also comprise a surface with at least one opening for mounting by the mounting bracket through the at least one opening at least the X-ray source, wherein the at least one opening is dimensioned so as to allow for the range of movement of the X-ray source as guided by said guiding construction.

The invention claimed is:

1. A dental or medical X-ray imaging apparatus, comprising:
    an X-ray detector;
    an X-ray source configured to generate X-ray irradiation and comprising a collimator construction functionally connected to the X-ray source, the collimator construction configured to limit the X-ray irradiation generated by the X-ray source into a beam to be aimed in the direction of the X-ray detector and defining an X-ray irradiation field pattern;
    a light field indicator comprising a visible light emitting construction and configured to project a visible light field pattern to be aimed in the direction of the X-ray detector;
    a control system, the control system comprising control information relating to an imaging mode;
    characterized in that the apparatus comprises a support construction to which the X-ray source, the X-ray detector and the visible light emitting construction are mounted and wherein the support construction is configured to enable positioning the X-ray source and the visible light emitting construction at essentially the same location in relation to the support construction, so as to when at a given time locating at said essentially same location to direct a given field pattern in essentially the same direction towards the X-ray detector, and further a first frame part extending in a first direction and comprising a first end and a second end and wherein the support construction to which the X-ray source, the X-ray detector and the visible light emitting construction are mounted extends from the first frame part in a second direction essentially at right angles to the first direction; and wherein the control system is configured to receive information from the light field indicator on the characteristics of the visible light pattern it projects and to convert said received information to information on how to control operation of the collimator construction so as to adjust the X-ray irradiation field pattern to at least substantially correspond to the size and shape of the area the projected visible light pattern indicates, and/or that the control system is configured to receive information from the collimator construction on the characteristics of the X-ray irradiation field pattern it limits and to convert said received information to information on how to control operation of the light field indicator so as to adjust the visible light field pattern to at least substantially correspond to the size and shape of the X-ray irradiation field pattern.

2. The apparatus according to claim 1, characterized in that the support construction comprises a ring-shaped structure, the ring-shaped structure comprising a ring-shaped gantry and a housing which houses at least said ring-shaped gantry.

3. The apparatus according to claim 2, characterized in that the housing comprises a surface with at least one opening for mounting by the mounting bracket through the at least one opening at least the X-ray source, wherein the at least one opening is dimensioned so as to allow for the range of movement of the X-ray source as guided by said guiding construction.

4. The apparatus according to claim 1, characterized in that said positioning of the X-ray source and the visible light emitting construction at essentially the same location includes arranging the X-ray source and the visible light emitting construction movable in a direction at right angles to both said first and second direction.

5. The apparatus according to claim 1, characterized in that the X-ray source, the collimator construction and the visible light emitting construction are arranged to be movable as a fixed assembly.

6. The apparatus according to claim 1, characterized in that the X-ray source and the visible light emitting construction are arranged to be movable as a fixed unit in relation to the collimator construction.

7. The apparatus according to claim 1, characterized in that the light field indicator is configured to generate the visible light field pattern such that the pattern is a substantially evenly illuminated area or comprises a pattern of light fields which as a combination indicates an area.

8. The apparatus according to claim 1, characterized in that the light field indicator is configured to enable projecting visible light field patterns of different sizes and/or different shapes, and the collimator construction is configured to enable limiting X-ray irradiation field patterns of different sizes and/or of different shapes.

9. The apparatus according to claim 1, characterized in that the control system comprises correlation information relating to dimensions of the visible light field pattern and the X-ray irradiation field pattern, at a given distance from the X-ray detector, and the light field indicator and the collimator construction are configured to enable adjusting dimensions and/or shape of their respective field patterns according to the correlation information such that the field patterns cover essentially the same area at said given distance from the X-ray detector, and/or wherein the correlation information includes correlation information relating to a given imaging mode.

10. The apparatus according to claim 9, characterized in that the given imaging mode is a CBCT imaging mode and the control system is configured to enable indicating by the visible light field pattern an area at a given distance from the X-ray detector relating to a volume which, regarding a given CBCT imaging mode and in case using a given collimation setting of the X-ray beam, will cover.

11. The apparatus according to claim 9, characterized in that the apparatus comprises a component or components configured to determine location and/or shape of an anatomy positioned for imaging, and the control system is then configured to be able adjust the X-ray beam collimation and/or the projected visible light pattern on the anatomy using that knowledge, said location and/or shape then defining said given distance from the X-ray detector.

12. The apparatus according to claim 1, characterized in that the apparatus comprises a first guiding construction mounted to the support construction, and wherein the X-ray source and the visible light emitting construction are mounted together as a fixed unit and the first guiding construction is configured to enable moving said fixed unit, a range of said movement comprising a base position and a first and a second extreme position, wherein the first guiding construction optionally comprises a carriage mounted to said fixed unit comprising the X-ray source and the visible light emitting construction, a range of said movement of the carriage comprising a base position and a first and a second extreme position.

13. The apparatus according to claim 12, characterized in that the first guiding construction comprises at least one guiding groove or rail on a side of the support construction and a mating construction on a side of the carriage.

14. The apparatus according to claim 13, characterized in that the first guiding construction comprises a motorized construction in functional connection with the carriage, the motorized construction providing said moving of the fixed unit comprising the X-ray source and the visible light emitting construction within said range comprising the first and second extreme positions.

15. The apparatus according to claim 12, characterized in that the first guiding construction includes a position sensor arrangement configured to acquire information relating to a position of said fixed unit comprising the X-ray source and the visible light emitting construction within said range of movement, the position sensor arrangement being configured to detect a position of the carriage within said range of movement of the carriage.

16. The apparatus according to claim 12, characterized in that the first guiding construction is configured to enable laterally moving said fixed unit and the motorized construction comprises a driving screw, the driving screw being aligned parallel with said at least one guiding groove or rail and arranged in functional connection with the carriage.

17. The apparatus according to claim 16, characterized in that the position sensor arrangement comprises a magnetic component structurally connected to the carriage and movably connected to a rod extending in parallel with said at least one guiding groove or rail and said driving screw of the guiding construction.

18. The apparatus according to claim 12, characterized in that a mounting bracket is fixed to the carriage and, on the other hand, to the fixed unit comprising the X-ray source and the visible light emitting construction, to mechanically connect said fixed unit to the guiding construction.

19. The apparatus according to claim 12, characterized in that a signal path is provided between the first guiding construction and the control system, the signal path comprises a signal path between the position sensor arrangement and the control system.

20. The apparatus according to claim 9, characterized in that a signal path is provided between the collimator construction and the control system, and between the light field indicator and the control system, to enable controlling the collimator construction and the light field indicator according to the correlation information.

* * * * *